United States Patent [19]

Evans et al.

[11] Patent Number: 4,804,802

[45] Date of Patent: * Feb. 14, 1989

[54] ISOMERIZATION PROCESS WITH RECYCLE OF MONO-METHYL-BRANCHED PARAFFINS AND NORMAL PARAFFINS

[75] Inventors: Wayne E. Evans; Stephen C. Stem, both of Houston, Tex.

[73] Assignee: Shell Oil Company, Houston, Tex.

[*] Notice: The portion of the term of this patent subsequent to Jan. 5, 2005 has been disclaimed.

[21] Appl. No.: 147,477

[22] Filed: Jan. 25, 1988

[51] Int. Cl.⁴ .............................................. C07C 5/27
[52] U.S. Cl. .................... 585/734; 585/738; 585/737; 585/820; 585/822; 208/310 Z
[58] Field of Search .......................... 208/310, 310 Z; 585/820, 738, 822, 737, 734

[56] References Cited

U.S. PATENT DOCUMENTS

| | | | |
|---|---|---|---|
| 2,935,539 | 5/1960 | Gladrow et al. | 585/739 X |
| 2,950,952 | 8/1960 | Breck et al. | 23/113 |
| 2,956,089 | 10/1960 | Mattox et al. | 585/821 X |
| 3,030,181 | 4/1962 | Milton | 23/113 |
| 3,706,813 | 12/1972 | Neuzic | 585/820 X |
| 3,755,144 | 8/1973 | Asselin | 208/95 |
| 3,836,455 | 9/1974 | Blytas | 208/310 |
| 4,176,053 | 11/1979 | Holcombe | 208/310 |
| 4,210,771 | 7/1980 | Holcombe et al. | 585/701 |
| 4,251,499 | 2/1981 | Nanne et al. | 423/329 |
| 4,309,281 | 1/1982 | Dessau | 585/820 X |
| 4,476,345 | 10/1984 | Gray, Jr. et al. | 585/820 |
| 4,717,784 | 1/1988 | Stem et al. | 585/739 X |

OTHER PUBLICATIONS

"Zeolites: Science and Technology", Rodriguez, Rollmann, and Naccacag.

"Industrial Application of Shape Selective Catalyst", Chen and Garwood.

Primary Examiner—Patrick P. Garvin
Assistant Examiner—George R. Fourson
Attorney, Agent, or Firm—Kimbley L. Muller

[57] ABSTRACT

This invention relates to a process for the production of an isomerate gasoline blending component where the octane value of the isomerate is increased relative to prior art processes utilizing single separatory sieves. After respective isomerization of feed streams comprising $C_6$ or $C_6+$ normal paraffins, a multiple separatory sieve is located to selectively adsorb unreacted normal paraffins and mono-methyl-branched paraffins from an isomerate product stream. The preferred first separatory sieve is exemplified by a calcium 5A sieve which can adsorb normal paraffins while allowing mono-methyl-branched paraffins and more higly branched paraffin to pass to a second separatory sieve. The second sieve comprises a shape-selective zeolite having a pore size intermediate $5.5 \times 5.5$ and $4.5 \times 4.5$A to selectively adsorb said mono-methyl-branched paraffins while allowing the more highly branched paraffins to pass through or along the separatory sieve and become the isomerate product blending component. The preferred second separatory molecular sieve is exemplified by a ferrierite which can adsorb methylpentane while allowing more highly branched materials such as 2,3-dimethylbutane to pass through or along the sieve. At least a portion of both the normal paraffin and the mono-methyl-branched paraffins are recycled to the isomerization zone of the process. The separatory sieves may be located in a vertical relationship (either upflow or downflow) or in a horizontal relationship.

22 Claims, 2 Drawing Sheets

ISOMERIZATION PROCESS WITH RECYCLE OF MONO-METHYL-BRANCHED PARAFFINS AND NORMAL PARAFFINS

FIELD OF THE INVENTION

This invention relates to a process for making an isomerate gasoline blending component with higher octane by increasing the relative proportion of di-methyl-branched paraffins in the isomerate while reducing the quantity of mono-methyl-branched paraffins in the isomerate. As a corollary, the field of this invention is concerned with the development of a unique recycle stream in an isomerization process having not only normal paraffins but also mono-methyl-branched paraffins (e.g., methylpentanes).

As a result of pollution and environmental problems, retail gasolines in the United States eventually will have a phase-down lead content. Maintenance of high octane gasolines by methods other than lead addition is of continuing interest to U.S. refiners. Two major techniques are available to acquire high octane gasoline pools without lead addition. First, hydrocarbons can be reformed in the presence of a reforming catalyst, such as a platinum rhenium catalyst, to a high octane gasoline. Second, normal paraffins can be isomerized to branched paraffins which possess high octane qualities. This invention concerns the latter of these two processes and is an improvement over standard isomerization processes. The process of this invention supplies a unique recycle stream to boost octane ratings of the isomerate gasoline blending component without the expense of additional hydrocarbon consumption.

From the standpoint of increasing octane, it is desirable that hydrocarbons in gasoline have maximum branching. For example, methylpentanes have lower octane ratings than do dimethylbutanes. Thus, in an isomerization process it is beneficial to maximize the content of dimethylbutanes (di-branched paraffins) even at the expense of methylpentanes (mono-methyl-paraffins). Applicants have discovered that a means to accomplish this goal is to formulate and develop an ideal recycle stream derivative of a combination of shape selective molecular sieves. This recycle stream is comprised not only of normal paraffins but also of mono-methyl-branched paraffins such as methylpentanes. The product stream of this isomerization process contains an increased production of dimethylbutanes, the most highly branched and highest octane of the $C_6$ saturates. This results in a direct octane enhancement to the resultant gasoline with only a small incremental increase in cost associated with recycling an increased volume. Moreover, in refineries which restrict production of gasoline due to octane limitations, this octane enhancement can be used to increase gasoline production.

BACKGROUND OF THE INVENTION

Pertinent areas of the classification manual concerned with this type of invention are, among others, Class 208, Subclass 310 and Class 585, Subclasses 820, 701 and 738. In Gray Jr. et al, U.S. Pat. No. 4,476,345, an invention is disclosed in which a portion of one of the product streams in an isomerization process is used to wash a recycle gas stream to improve the quality of the isomerate products. The molecular sieve adsorbent of Gray is one which can be naturally occurring or synthetically produced comprising a three-dimensional crystalline-zeolitic aluminosilicate which will selectively, on the basis of molecular size of the pores, adsorb normal paraffins from the isomerized product from branched chained and/or cyclic paraffins. The molecular sieves have pore diameters of about 5 Å and are exemplified by Zeolite A, specifically calcium 5A, which exhibits pore diameters ranging from about 3 to about 5 Å. The teachings of this patent are herein incorporated by reference in regard to one of the molecular sieves of this invention which functions to selectively remove the normal paraffins from the other two paraffinic species, i.e., mono-methyl-branched paraffins and di-branched paraffins.

The Gray et al disclosure is an improvement upon an isomerization process as taught in Holcombe, U.S. Pat. No. 4,210,771. This is a process for the virtually complete isomerization of normal paraffin hydrocarbons in a feed stream consisting essentially of mixed normal and branched hydrocarbons, where the feed stream is passed first through an isomerization reactor and the products derived therefrom are passed to an adsorption section which separates normal from branched paraffins to form an isomerate having both di- and mono-branched paraffins. A recycle stream comprising nearly pure normal paraffins is usually recycled to exhaustion. Other disclosures which may be commensurate with Holcombe comprise U.K. Pat. No. 876,730 and U.S. Pat. No. 3,755,144 issued to Asselin.

The zeolitic molecular sieve employed in Gray et al and Holcombe may be selected from any adsorbent which selectively adsorbs normal paraffins based on the molecular pore size of the aluminosilicate. A particularly suitable zeolite of this type is a calcium exchanged A zeolite. Naturally occurring zeolite molecular sieves which could be substituted for calcium exchanged A zeolite include chabazite and erionite. The particular flow scheme of adsorption as taught by Holcombe U.S. Pat. No. 4,210,771 is herein incorporated by reference to show an operable multiple zeolite molecular sieve absorption means, to achieve proper adsorption-fill and desorption-purge. The Holcombe patent is completely silent as to arrangements of a multiple number of different sieves which may be present in the absorption separation technique. In fact, in the drawing of Holcombe, the adsorption bed systems, 44, 46, 48, and 50, are all comprised of a calcium 5A zeolite in the form of 1/16-inch cylindrical pellets. Branched paraffins, whether they be mono- or di-branched, flow through the adsorption bed while unbranched normal paraffins are adsorbed. After a purge of the adsorbed normal paraffins from the zeolite molecular sieve, the recycle stream is comprised nearly entirely of normal paraffins and recycle hydrogen. This is mixed with the incoming feed before charge to the isomerization zone.

A second Holcombe patent, U.S. Pat. No. 4,176,053, discusses a normal paraffin-isomerization separation process. By this technique, normal paraffins are isolated from a feedstock mixture comprising normal and branched paraffins at super atmospheric pressures using an adsorption system comprising at least four fixed adsorbent beds containing a calcium 5A molecular sieve. A stream is formed comprising vapor from void space purgings of the adsorbent and feedstock containing iso-paraffins and normal paraffins. The molecular sieve employed to separate normal paraffins from said stream is selected to adsorb only normal paraffins from a mixture of branched, cyclic and normal hydrocarbons in order to segregate the normal paraffins from the mixture and provide a normal paraffin recycle stream to insure isomerization of the normal paraffins to exhaustion.

In U.S. Pat. No. 3,836,455 issued to Blytas, the separation of methylpentane and 2,2-dimethylbutane (as contrasted with 2,3-dimethylbutane of the instant invention) is accomplished using an offretite zeolite. U.S. Pat. No. 4,251,499 issued to Nanne et al teaches that ferrierite sieves are effective for dividing substantially unbranched structures (n-paraffins) from mixtures of same (n-paraffins) with branched structures (both mono-methyl and di-branched paraffins). Such was the state of the art in 1981 although the instant invention has shown that this teaching is no longer accurate in regard to the adsorption capacity of ferrierite aluminosilicates.

These patents teach that it is most advantageous to recycle normal paraffins to thereby isomerize the same to the isomerate components comprising mono-methyl-branched paraffins and di-branched paraffins. These disclosures suggest that the isomerate will have a certain quantity of mono-methyl-branched paraffins derived from the isomerization zone. These mono-methyl-branched paraffins will indigenously have an inherently lower octane value than the di-branched paraffins.

In contrast, applicants have discovered a new and more efficient isomerization process utilizing a multiple number of molecular sieves whereby both normal paraffins and mono-methyl-branched paraffins are recycled to increase the relative quantity of di-branched paraffins in the isomerate. Using the specific multiple molecular sieve separation technique of this process, mono-methyl-branched paraffins are diminished in the isomerate and substantially increased in the recycle stream. In other words, this process increases the degree of branching existing within the isomerate by increasing the quantity of mono-methyl-branched paraffins in the recycle stream.

In summary, the select combinative molecular sieve separation zone of this invention comprises a first molecular sieve which will adsorb normal paraffins and a second molecular sieve which will adsorb normal paraffins and mono-methyl-branched paraffins. The separatory molecular sieves of the above cited patentees (except for U.S. Pat. No. 3,836,455 issued to Blytas) adsorb only normal paraffins while allowing mono-methyl-branched paraffins to remain and commingle with the isomerate product stream. Finally, neither of the two select molecular sieves of this invention adsorbs 2,3-dimethylbutane, which is passed to the isomerate product stream as a select octane blending component for gasoline. In Blytas, on the other hand, a process is disclosed which is based on offretite which excludes 2,2-dimethylbutane but has a channel size which is too large to distinguish between methylpentane and 2,3-dimethylbutane.

OBJECTS AND EMBODIMENTS OF THE INVENTION

An object of this invention is to provide a process with a recycle stream to an isomerization process wherein both normal paraffins and mono-methyl-branched paraffins are recycled to the isomerization zone.

Another object of this invention is to provide a total isomerization product with a mixumum content of di-methyl-branched paraffins such as 2,3-dimethylbutane.

Another object of this invention is to provide a unique application of a select combination of molecular sieves to achieve a more exact separation of normal paraffins and mono-methyl-branched paraffins from di-methyl-branched paraffins.

Yet another object of this invention is to provide an isomerization process able to attain an isomerate (product stream) of higher octane value than previously recognized.

Yet another object of this invention is to provide a process wherein normal hexane is isomerized to an isomerate product having an increased quantity of dimethylbutane and a decreased quantity of methylpentanes utilizing a select combination of molecular sieves, one having a pore size sufficient to adsorb normal paraffins and another having a pore size sufficient to adsorb normal paraffins and mono-methyl-branched paraffins. Both select sieves will not adsorb di-methyl-branched paraffins.

An embodiment of this invention resides in a process for the isomerization of $C_6$ normal paraffins or mixtures of normal paraffins larger than $C_6$ to produce a gasoline blending component comprising di-branched paraffins which comprise: passing said paraffins or mixture of paraffins to an isomerization zone maintained at isomerization conditions and containing an isomerization catalyst to isomerize said $C_6$ normal paraffin, or mixture of normal paraffins and recycle stream of normal and mono-methyl-branched paraffins passed to said isomerization zone and thereby produce an isomerization zone effluent stream comprising di-branched paraffins, mono-methyl-branched paraffins and unreacted normal paraffins; passing said isomerization zone effluent stream to a separation zone comprising multiple shape-selective molecular sieves arranged in a series flow path such that the isomerization zone effluent stream passes through a first shape-selective molecular sieve and then passes through a second shape-selective molecular sieve, wherein said multiple step passage comprises: (i) a first molecular sieve having a pore size of 4.5 A or less and being effective to adsorb n-paraffins and effective to restrict adsorption of mono-methyl-branched paraffins and di-branched paraffins; and (ii) a second molecular sieve having a pore size intermediate $5.5 \times 5.5$ and $4.5 \times 4.5$ A but excluding $4.5 \times 4.5$ A and being effective to adsorb n-paraffins and mono-methyl-branched paraffins and effective to restrict adsorption of di-branched paraffins; separating said normal paraffins from said mono-methyl-branched paraffins in said first molecular sieve separation of step (i) and separating said mono-methyl-branched paraffins from said di-branched paraffins in said second molecular sieve of step (ii), recycling at least a portion of said n-paraffins and said mono-methyl-branched paraffins to said isomerization zone, and recovering said di-branched paraffins as said gasoline blending component.

BRIEF DESCRIPTION OF THE INVENTION

This invention is concerned with a novel separation zone downstream of an isomerization conversion having multiple shape-selective separatory sieves to permit formation of a recycle stream comprising normal paraffins and mono-methyl-branched paraffins. The multiple separatory sieves must be placed in a certain order to have an operable process. The first separatory sieve has a pore size smaller than or equal to $4.5 \times 4.5$ A to adsorb normal paraffins while allowing mono-methyl-branched paraffins and di-branched paraffins to pass through the sieve. The second sieve is a molecular sieve having a pore size intermediate 5.5×5.5 to 4.5×4.5 A but excluding 4.5×4.5 A which will adsorb the mono-methyl-branched paraffins while allowing the dimethyl paraffins to pass through the sieve and be collected as the isomerate product stream.

DETAILED DESCRIPTION OF THE INVENTION

The contemplated feedstreams to this isomerization process are comprised mainly of isomeric forms of saturated hydrocarbon having $C_6$ or greater carbon atoms. Preferably, the mixture comprises mainly normal hexane. The mixtures can also comprise many $C_6^+$ normal paraffins such as normal heptane, normal octane, normal nonane, normal decane, etc. Such feedstreams are usually derived from refinery operation and contain quantities of $C_5^-$ and $C_7^+$ aliphatic paraffins and cyclic paraffins. Olefinic and aromatic hydrocarbons may also be present. A preferred feedstream will contain more than 25 mole percent normal hexane.

The selected feed material is passed through an isomerization zone containing an isomerization catalyst. The isomerization catalyst is preferably a zeolite with a catalytic metal dispersed thereon. Exemplary of said catalyst is mordenite dispersed thereon with platinum in a range of from about 0.005 wt % to about 10.0 wt % platinum with a preferred range being from about 0.2 wt % to about 0.4 wt % platinum. Other zeolite molecular sieves are also available which have a silica to alumina molar ratio of greater than 3 but less than 60 and preferably less than 15. These zeolite molecular sieves have many polyvalent cations exchanged with the sieve, such as those of the alkali or alkaline earth metals. The catalytic metals associated with the isomerization mechanism are preferably noble metals selected from Group VIII of the Periodic Table of Elements as exemplified by platinum, palladium, osmium, and ruthenium, etc. The isomerization catalyst can be present per se or it can be mixed with a binder material such as cellulose. Other equivalent isomerization catalysts can be utilized within the confines of this invention, however, the mordenite-Group VIII metal catalyst is most preferred. A faujausite molecular sieve may also be utilized but usually has poorer selectivity than mordenite.

The isomerization conditions present in the isomerization zone are selected to maximize the conversion of normal paraffins to mono-methyl-branched paraffins and di-branched paraffins. The isomerization reactions are favored in the vapor phase with a fixed bed of isomerization catalyst although isomerization can also be accomplished in the liquid phase. Typical isomerization operating conditions include a temperature of from about 200° C. to about 400° C. and a pressure of about 10 to 40 bar. The isomerization process, which is limited in octane upgrading by thermodynamic equilibrium, is frequently measured at 10 points. Even at these select conditions, the effluent from the isomerization reactor will contain a substantial amount of normal paraffins, i.e., 20-30 wt %, and mono-methyl-branched paraffins which are unreacted or partially reacted due to the aforementioned equilibrium.

After isomerization, the isomerization zone effluent is transmitted to a separation zone. The term isomerization zone effluent stream denotes the discharge from the isomerization zone containing normal paraffins, mono-methyl-branched paraffins and di-branched paraffins. In contrast, the term isomerate product stream denotes the isomerate derived from the separatory sieve, which is predominantly di-branched paraffins. The separation zone will comprise at least two shape-selective molecular sieves, which can be included in a single adsorbent bed or can comprise from about 2 to about 20 adsorbent beds and will be operated in an adsorption/desorption mode as exemplified in U.S. Pat. No. 4,210,771. The two molecular sieves have differing functions. It is critical which sieve initially separates the isomerization zone effluent stream.

The first shape-selective molecular sieve must be one effective to adsorb normal paraffins while allowing mono-methyl-branched paraffins and di-branched paraffins to pass to a second molecular sieve. Said first molecular sieve will have an apparent pore diameter of 4.5 A or less. A particularly suitable first molecular sieve is a calcium 5A sieve as described in U.S. Pat. No. 2,883,243 although other divalent exchanged forms of the sieve may also be utilized. With proper choice of the pore sizes the first molecular sieve can be an aluminophosphate, a silicoaluminophosphate or a tectosilicate like, for example, a borosilicate. Other molecular sieves will include the zeolite-R as exemplified in U.S. Pat. No. 3,030,181 or zeolite-T as exemplified in U.S. Pat. No. 2,950,952. It is also foreseeable that the aluminosilicate sieve can be a naturally occurring zeolitic molecular sieve such as chabazite or erionite. The critical dimension of the sieve is the pore diameter existent in the sieve. With a pore diameter of 4.5 A, but not larger, the normal paraffins will be adsorbed and allow the mono-methyl-branched paraffins and di-branched paraffins to pass through the first sieve to a second shape-selective sieve.

The second shape-selective molecular sieve preferably has channel dimensions intermediate a calcium 5A sieve and a ZSM-5 sieve. The second molecular sieve is capable of adsorbing both normal hexane (if any remains after the adsorption of the first sieve) and methylpentanes as well. A preferred second molecular sieve of this invention comprises a tectosilicate having 8 and 10 member rings and having a pore diameter intermediate 5.5×5.5 and 4.5×4.5 A but excluding 4.5×4.5 A.

The most preferred second tectosilicate sieve is ferrierite which exhibits greatly increased adsorption capacity towards methylpentanes relative to a calcium 5A molecular sieve. Both the hydrogen and sodium form of ferrierite are viable sieves although it is preferred that the ferrierite be utilized after exchange with a cation of an alkali metal, alkaline earth metal, or transition metal cation. The second shape-selective molecular sieves of this invention include ferrierite and other analogous shape-selective materials with channel dimensions intermediate those of a calcium 5A and ZSM-5 molecular sieves which selectively adsorb normal pentanes and methylpentanes while dimethylbutanes are excluded.

Other examples of crystalline sieves which may be utilized to adsorb the normal paraffins and mono-methyl-branched paraffins include aluminophosphates, silicoaluminophosphates and tectosilicates like, for example, borosilicates. These shape-selective sieves are given as examples of the type of molecular sieves suitable as a first sieve. They may also be suitable as a second sieve. Pore sizing is critical to adsorption; the particular aluminophosphate, silicoaluminophosphate or tectosilicate, can be used as the species of either the first or second sieve as long as they are properly sized to attain the preferential adsorptions.

It is feasible that the instant shape-selective molecular sieve could begin as a large pore zeolite but the ion exchanged with large cations to diminish the ultimate channel size of the sieve to be within the aforementioned range of dimensions. Any molecular sieve having channel dimensions intermediate those of 5.5×5.5 and 4.5×4.5 A will have the potential to differentiate between methylpentanes and dimethylbutanes. This includes the aforementioned aluminophosphates, silicoaluminophosphates and tectosilicates as potential sieves. These sieves can be eight and ten member ring molecular sieves with the chosen pore size dimensions of this invention. The following list is presented which shows the requisite type of sieves which are viable as the second molecular sieve.

TABLE 1

| Molecular Sieve | Channel Dimensions (Å) | Size |
| --- | --- | --- |
| chabazite | 3.9 × 4.1 | TOO SMALL |
| zeolite A | 3.9 × 4.1 | TOO SMALL |
| erionite | 3.6 × 5.2 | TOO SMALL |
| Ca-5A | 4.5 × 4.5 | TOO SMALL |
| aluminosilicate ferrierite | 4.5 × 5.5 | CORRECT SIZE |
| aluminophosphate | 4.5 × 5.5 | CORRECT SIZE |
| silicoaluminophosphate | 4.5 × 5.5 | CORRECT SIZE |
| borosilicate | 4.5 × 5.5 | CORRECT SIZE |
| ZSM-5 | 5.4 × 5.6 | TOO LARGE |
| offretite | 6.0 × 6.0 | TOO LARGE |
| mordenite | 6.7 × 7.0 | TOO LARGE |
| omega | 7.4 × 7.4 | TOO LARGE |
| Y zeolite | 7.4 × 7.4 | TOO LARGE |

Molecular sieves that are too small in pore size do not discriminate between the mono-methyl-branched $C_6$ (i.e., methylpentanes) and di-methyl-branched $C_6$ (i.e., dimethylbutanes). In fact, they exclude both. Molecular sieves that are listed as too large do not discriminate between mono-methyl-branched and 2,3-di-methyl-branched $C_6$ paraffins. In fact, they adsorb them. Only molecular sieves between, and not including, the sizes of the sieves of the calcium 5A and ZSM-5 will discriminate to accommodate adsorption of the mono-methyl-branched paraffins in addition to normal paraffins while excluding the 2,3-di-methyl-branched $C_6$ paraffins. And only these molecular sieves are adequate as the second adsorbent. While ferrierite is the best example of such a second separatory sieve, this invention should not be limited to ferrierite per se as the only shape-selective species suitable as the second sieve.

A ferrierite-type molecular sieve having dimensions between 5.5×5.5 and 4.5×4.5 A could be used to adsorb both normal paraffins and mono-methyl-branched paraffins without the necessity of the smaller pore sieve of the instant invention (e.g., calcium 5A). However, with the ferrierite-type sieve as the sole molecular sieve, a major element of economy is sacrificed. The two combinative molecular sieve bed of the instant invention necessitates a much lower overall volume of molecular sieve than if the bed were comprised solely of ferrierite. This is because the calcium 5A sieve has a much greater adsorption capacity for normal paraffin adsorption than does ferrierite.

Furthermore, if the two molecular sieves which comprise the instant invention are segregated into separate vessels, it then becomes the option of the process operator whether to produce isomerate product utilizing a conventional recycle stream of only n-paraffins or whether to employ the instant invention and recycle mono-methyl-paraffins as well as normal paraffins. If a molecular sieve bed is comprised solely of ferrierite to produce the recycle stream (containing mono-methyl-paraffins), operator flexibility is sacrificed. The instant combinative molecular sieves reduces sieve volume while providing an increase in operator flexibility.

The sequential placement of the two molecular sieves is critical to this invention. The ferrierite type sieve having dimensions between 5.5×5.5 and 4.5×4.5 A cannot be utilized first in the sequence. The first sieve must be the smaller pore sieve exemplified by the calcium 5A zeolite which adsorbs normal paraffins but will adsorb only negligible amounts of mono-methyl-branched paraffins. If a stacked bed placement of the two sieves is contemplated, the relative quantities of the two sieves would be that quantity wherein break-through time of normal paraffins from the first (i.e., calcium 5A) sieve equals the break-through time of the mono-methyl-branched paraffins from the second sieve. In other words, both sieves become saturated at the same time, the first sieve with normal paraffins and the second sieve with mono-methyl-branched paraffins. In the event that the sieves are placed in an integral vessel, there will probably be but one recycle stream containing both normal paraffins and the mono-methyl-paraffins, e.g., methylpentanes. It is however possible that a dual functional recycle stream can be developed wherein desorption from the first separatory sieve, e.g. calcium 5A, comprises a select normal paraffin recycle while the recycle stream derived from the second sieve, e.g. ferrierite, comprises mainly methylpentanes with some small portion of normal paraffins which were not removed in the first sieve. Both of these recycle streams may be combined or individually passed to either the isomerization zone or to the charge stream feeding the isomerization zone.

In the event that the sieves are contained in segregated vessels, break-through of the particular normal paraffins and methylpentanes can be reached individually and the relative sieve volume chosen in any manner. It is also preferred that if the sieves are contained in multiple vessels, that a multiple number of dual sieves be provided to permit continuous processing of the isomerization zone effluent stream while desorbing and regenerating spent adsorbent. In this embodiment a normal paraffin break-through point is realized in the conduit connecting the first sieve with the second separatory sieve. At this point normal paraffin is being recycled to the isomerization zone while the second molecular sieve is adsorbing the methylpentanes while allowing di-branched isomerate to accumulate downstream of the second sieve bed.

A suitable valving system can be arranged to provide that, once the initial calcium 5A-like sieve becomes saturated with normal paraffins, a next calcium 5A-like sieve is employed with conduits such that the substantially normal paraffin-free effluent from the first separation zone will still pass downstream to the second molecular sieve separation zone. Downstream of the latter, a methylpentanes break-through point is reached when a flow of methylpentanes indicates that this ferrierite-like sieve has reached full saturation. At this time the initial sieve is taken out of service and a substitute ferrierite-like sieve is utilized to treat the methylpentane and di-branched paraffin effluent from the first separation zone. A recycle stream of mono-methyl paraffins, i.e. methylpentanes, is recycled from the second sieve to the isomerization zone along with any normal paraffins which are derived from the second, ferrierite-like sieve.

This stream can be combined with the recycle stream derived from the first, calcium 5A-like sieve comprising mainly normal paraffins.

The adsorption/desorption condition present in the separation zone will include a temperature from about 75° C. to about 400° C. and a pressure from about 2 bar to about 50 bar. A specific desorbent utilized to extract the trapped normal paraffins and mono-methyl-branched paraffins from the sieve can comprise hydrogen or steam, which can be passed along with the normal paraffins and mono-methyl-branched paraffins as a component of the recycle stream to the isomerization zone.

DETAILED DESCRIPTION OF THE DRAWINGS

Figure 1:
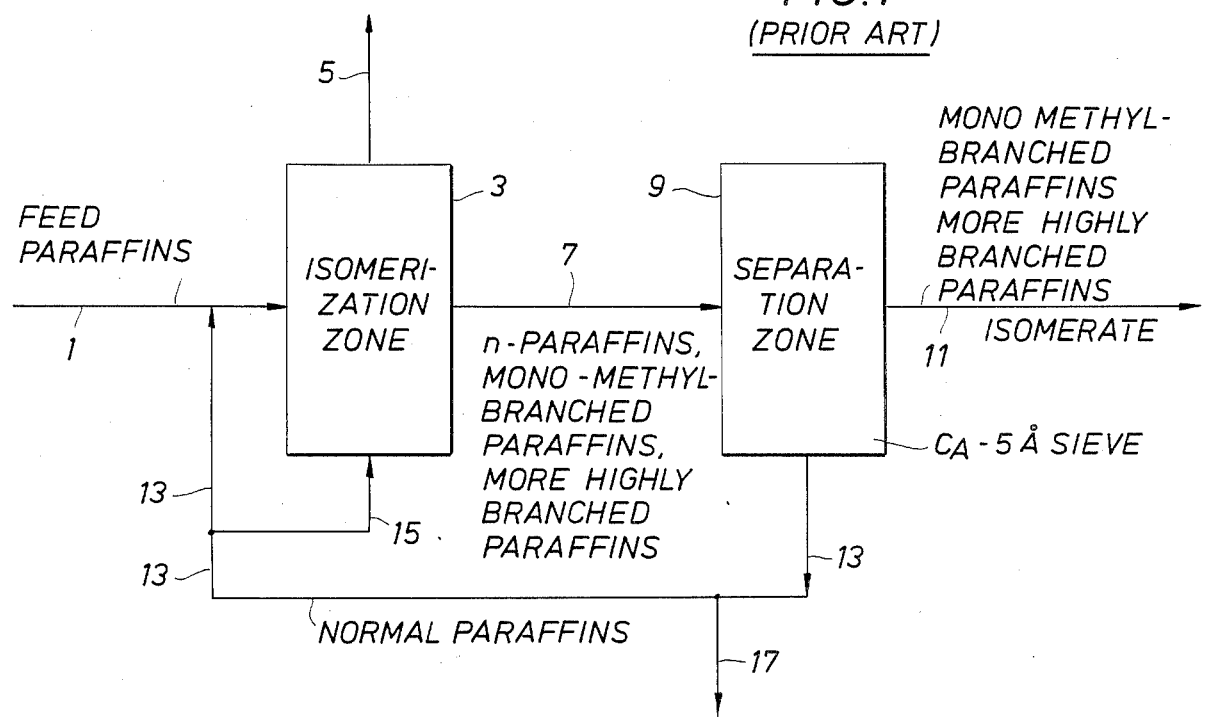
FIG. 1 is a schematic flow scheme of an isomerization process as established in the prior art.

In FIG. 1 a feedstream comprising a fresh feed having, for example, 4 mole % $C_1$ to $C_5$ and 93 mole % $C_6$ paraffins with minute quantities of cycloparaffins, aromatics and $C_7^+$ paraffins is passed through conduit 1 into isomerization zone 3. This zone is maintained at conditions selective to maximize production of branched paraffins from the feed material. An isomerization zone effluent adsorbent such as a Ca5A aluminosilicate, which is described in U.S. Pat. No. 4,210,771, is present to perform the separation of normal paraffins from both mono-methyl-branched paraffins and more highly branched paraffins. If desirable, a hydrogen gas or a light hydrocarbon gas can be vented from isomerization zone 3 by means of conduit 5. An effluent stream from isomerization zone 3 is removed in conduit 7 containing normal paraffins, mono-methyl-branched paraffins and more highly branched paraffins (for example, ethylpentane, dimethylbutane, etc.). All of these components are transmitted to separation zone 9 having at least three and preferably up to eight adsorbent beds of a singular and unitary molecular sieve such as a calcium 5A zeolite to separate isomerate product from recycle. The calcium 5A sieve will entrap or adsorb normal paraffins while allowing mono-methyl-branched paraffins and other branched paraffins to pass through the separation zone and be recovered in conduit 11 as the desirable isomerate. After applicable desorption, with means not shown, a normal paraffin stream in conduit 13 is withdrawn from separatory zone 9 and passed either to admixture with feed in conduit 1 or a portion of the same is transmitted to isomerization zone 3 by means of conduit 15. It is preferred that some type of slipstream be present in the recycle stream as shown in conduit 17 to eliminate unwanted impurities and to remove certain normal paraffins (e.g. propane) if they cannot be isomerized to exhaustion.

Figure 2:
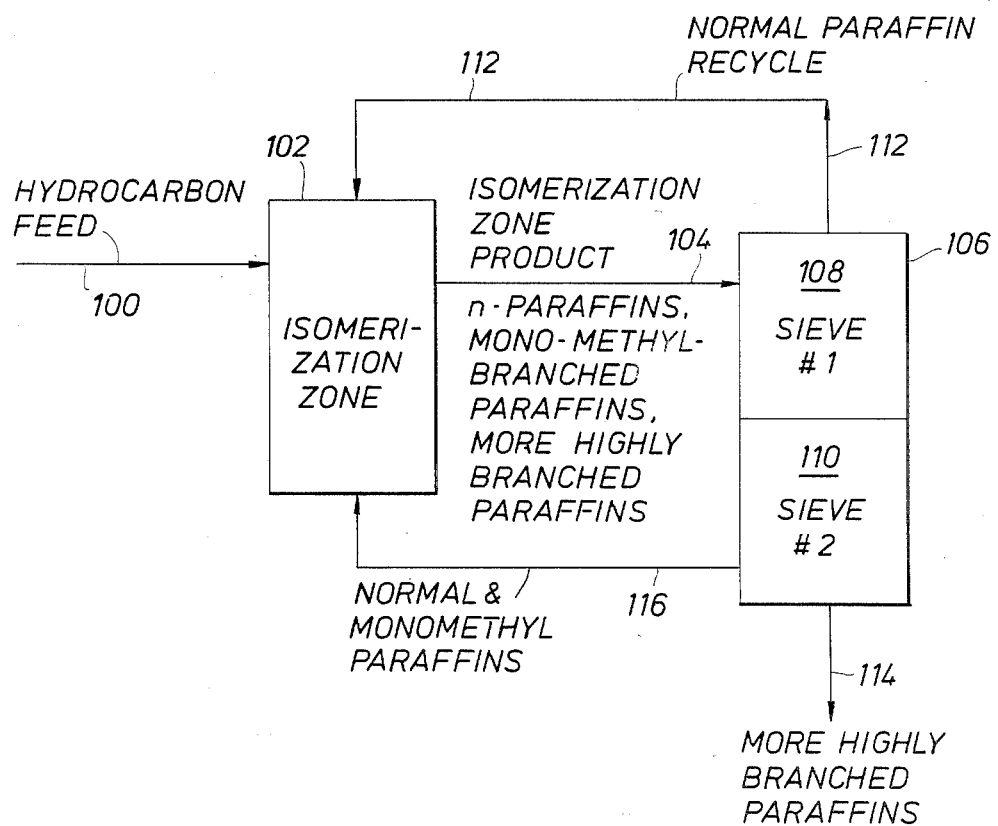
FIG. 2 is a schematic flow scheme of the novel process of this invention where the aluminosilicate sieve first contacted by the isomerization zone effluent is of a pore size dimension of less than or equal to 4.5 A and where the sieves are contained in a unitary vessel.

FIG. 2 represents a flow scheme where the first separatory molecular sieve comprises a sieve with a pore diameter equal to 4.5 Å or smaller in which normal paraffins are adsorbed while mono-methyl-branched paraffins and di-branched paraffins are not adsorbed. Both sieves are contained in a unitary vessel. In FIG. 2 a feed material similar to that described in regard to FIG. 1 is passed in conduit 100 to isomerization zone 102. In isomerization zone 102, an isomerization catalyst such as mordenite with platinum dispersed thereon, is effective to isomerize the feed paraffins to mono-methyl-branched paraffins and di-branched paraffins which are removed from isomerization zone 102 by means of a conduit 104. Because of the chemical equilibrium during isomerization, isomerization effluent stream 104 contains a significantly large portion of normal paraffins, which were not isomerized to branched chain paraffins in isomerization zone 102. It is important to acquire an isomerate having the highest octane value, i.e., the greatest extent of branching, and therefore the presence of normal paraffins and mono-methyl-branched paraffins in the isomerate product stream is undesirable.

In this embodiment, the normal paraffins, mono-methyl-branched paraffins, and di-branched paraffins are passed to separation zone 106 containing at least two shape-selective molecular sieves, 108 and 110. Molecular sieve 108 possesses a pore size of 4.5 Å or smaller. A particular species of this type of sieve is exemplified by a calcium 5A molecular sieve. This sieve is selective for the adsorption of normal paraffins while mono-methyl-branched paraffins and di-branched paraffins are freely passed to the second shape-selective molecular sieve 110. After proper desorption, a recycle stream of normal paraffins is removed from sieve 108 in conduit 112 and at least a portion is returned to isomerization zone 102 as a recycle stream.

The molecular sieve in zone 110 operates to adsorb mono-methyl-branched paraffins, and any other normal paraffins remaining after passage through adsorption zone 108, and thereby produce an isomerate having a relatively large amount of di-branched chain paraffins. This isomerate is removed from adsorption zone 110 in conduit 114. After proper desorption, at least a portion of the mono-methyl-branched paraffins, and any normal paraffins which are removed from zone 110, are recycled to isomerization zone 102 in conduit 116. It is within the confines of this invention that conduits 112 and 116 are combined to form a unitary recycle stream which may be added either to isomerization zone 102 or to feed paraffin charge conduit 100.

In this embodiment separatory sieves 108 and 110 are confined within a unitary vessel. It is preferred that these sieves be designed so that common break-through occurs simultaneously. That is, as sieve 108 becomes saturated with normal paraffins, sieve 110 will likewise become saturated with mono-methyl-paraffins and therefore both can be purged (i.e., subjected to a desorption cycle) at the same time. It is also preferred that a multiple number of these sieves 108 and 110 be present in parallel flow arrangement to provide that when one sieve is being purged another is being utilized for its separatory function.

Figure 3:
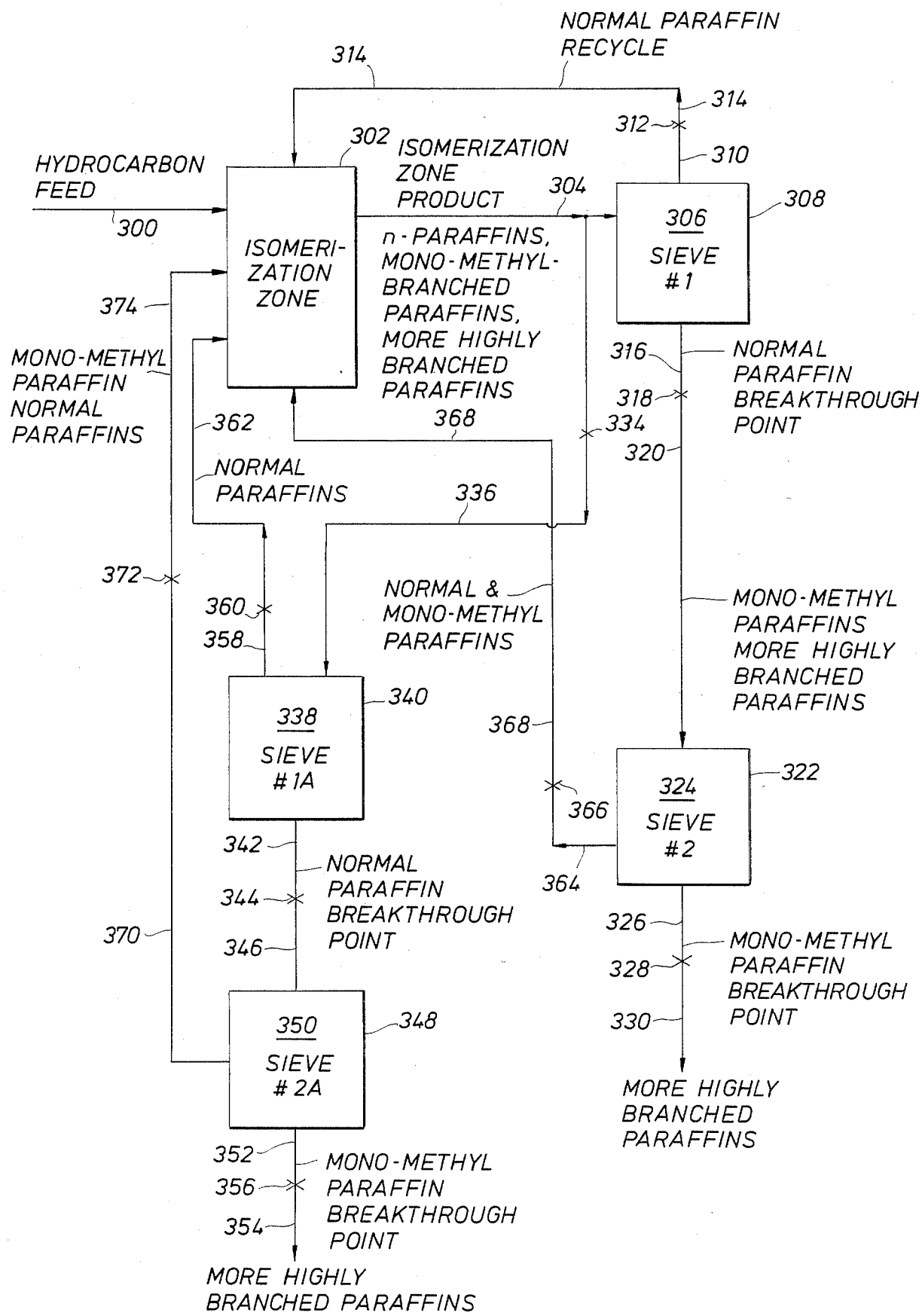
FIG. 3 is a schematic flow scheme of the novel process of this invention where the first aluminosilicate sieve has a pore size dimension of less than or equal to 4.5 A and where the respective sieves are contained in discrete vessels.

In FIG. 3 a second embodiment of this invention is shown having two molecular sieves in sequential arrangement but with each acting independent of one another. A hydrocarbon feed similar to that described in regard to FIG. 1 is added to isomerization zone 302 through conduit 300. In isomerization zone 302 normal paraffins are converted to mono-methyl-branched paraffins and di-branched paraffins. Because of the equilibrium of the isomerization reaction, there is a good percentage of the isomerization zone effluent discharge from isomerization zone 302 in conduit 304 containing normal paraffins. This effluent stream is passed to the first shape-selective molecular sieve 306 (sieve #1) contained within separation zone 308. This sieve is preferably a calcium 5A sieve which will adsorb normal paraffins to the exclusion of mono-methyl-branched paraffins and di-branched paraffins. The adsorbed normal paraffins are withdrawn from separation zone 308 in conduit 310, passed through valve 312 and recycled, at least in part, to isomerization zone 302 by conduit 314.

The effluent of the first separation zone 308 is removed in conduit 316 through valve 318 and conduit 320 and passed through seckond separation zone 322 containing separatory adsorbent 324 (sieve #2). It is preferred that this separatory adsorbent is a ferrierite composition exemplary of other shape-selective zeolites having a pore size of 5.5×5.5 to 4.5×4.5 A. This separatory sieve acts on the first separation zone effluent to adsorb mono-methyl paraffins and thereby produce a dibranched isomerate removed in conduit 326 through valve 328, which accumulates in a container (not shown) connected to conduit 330. This stream is referred to as the isomerate product stream (in addition to stream 352) and will also contain non-mono-methyl branched paraffins like ethylpentane.

Conduits 316 and 326 can be suited with means in order to determine break-through for the respective normal paraffin and mono-methyl-paraffin from respective molecular sieves 306 and 324. At a point in time, when the normal paraffin break-through is realized in conduit 316, i.e. normal paraffin is present in conduit 316, then valve 318 is closed and the effluent from isomerization zone 302 in conduit 304 is passed through valve 334 in conduit 336 into alternative sieve bed 338 (sieve 190 1A). This sieve is preferably the same composition as sieve 306 and most preferably is comprised of a calcium 5A zeolite. A similar normal paraffin breakthrough is achieved in conduit 342 similar to that acquired in conduit 316. At this time valve 344 is closed along with valve 334; the isomerization zone effluent stream in conduit 304 is once again treated by sieve 306 in separation zone 308 to adsorb the normal paraffins. Until the normal paraffin break-through is achieved in conduit 342, mono-methyl-paraffins and di-branched paraffins are passed to sieve zone 348 containing sieve 350 (sieve #2A) which is similar in composition to sieve 324.

In this manner di-branched paraffins can be recovered in conduits 352 and 354 by means of valve 356 as a second portion of the isomerate product stream. A mono-methyl-paraffin break-through is eventually realized in conduit 352 similar to the mono-methyl-paraffin break through point attained in conduit 326. At this time alternative sieves 338 and 350 are taken out of service and desorbed while sieves 306 and 324 function to treat the isomerization zone effluent stream.

A normal paraffin recycle stream can be derived from sieve 338 (after desorption) in conduit 358, and passed to isomerization zone 302 by means of valve 360 and conduit 362. This is very similar to the arrangement established in recycle conduit 310, valve 312 and conduit 314. At least a portion of the mono-methyl-paraffins are recycled from sieves 324 and 350 to the isomerization zone. This is accomplished from sieve 324 by means of conduit 364, valve 366 and conduit 368. The recycle of the mono-methyl-paraffins from sieve 350 is accomplished by means of conduit 380, valve 372 and conduit 374. In all of these recycle conduits there can be some normal paraffins present which will be adsorbed by shape-selective molecular sieves 324 and 350 provided that they survive adsorption in respective sieves 306 and 338.

It is contemplated that any number of sequential sieves such as (306–324) and (338–350), be arranged in a continuous processing sequence to facilitate the timely desorption of the adsorbed components in the sieves. FIGS. 2 and 3 are provided as a schematic flow scheme of this process and should not be construed as an undue limitation upon the claims as hereinafter set forth.

ILLUSTRATIVE EMBODIMENTS

Two examples are provided to show the advantage of a stacked bed system over a system containing solely a calcium 5A or solely a hydrogen ferrierite adsorbent. The product stream was defined to first consist solely of 2,3-dimethylbutane and second to consist of all branched material such as 2,3-dimethylbutane plus 3-methyl pentane. The feed material was an equimolar mixture of normal hexane, 3-methylpentane and 2,3-dimethylbutane.

Example 1

In this example three different adsorbent beds were utilized to treat an isomerization effluent containing equimolar amount of n-hexane, 3-methylpentane (3MP) and 2,3-dimethylbutane (23DMB). The adsorbent beds consisted of (1) all calcium 5A sieve, (2) all hydrogen ferrierite, and (3) a stacked bed of calcium 5A sieve followed by hydrogen ferrierite. In order to remove and recycle the n-hexane and 3MP from the isomerization effluent stream to a degree sufficient to produce 1.0 grams of essentially pure 23DMB in the isomerate product stream, a certain bed size was necessary for each type of bed. Table II demonstrates those bed sizes. It should be noted that the stacked bed system is nearly twice as effective as the hydrogen ferrierite bed system. That is, to produce the same quality of isomerate product, less than half as much stacked bed volume is required as compared to hydrogen ferrierite alone. And the hydrogen ferrierite bed system was over eight times more effective than the calcium 5A adsorbent alone.

In the stacked bed configuration, ferrierite adsorbs the 3-methylpentane in the absence of normal hexane, thus avoiding a competition between the isomers. The ratio of the calcium 5A to ferrierite should be chosen such that the calcium 5A sieve becomes saturated with normal hexane at the same time the ferrierite section becomes saturated with 3-methylpentane. For this experiment the ratio was about 80% hydrogen ferrierite and 20% calcium 5A.

TABLE II

| If requirement is an isomerate product stream of pure 23DMB | | | |
|---|---|---|---|
| | Ca-5A | H Ferrierite | Ca-5A/H-Ferr (1:4 Wt Ratio) |
| Quantity of Sieve Required | >500 g | 60 g | 36 g |

Example 2

In this example the requirement of the isomerate product stream was defined as an all-branched material, i.e., 2,3-dimethylbutane and 3-methylpentane, starting with the same feed as was used in Example 1, i.e., an equimolar mixture of n-hexane, 3MP and 23DMB. This example differs from Example 1 in that, in the former example, isomerate product quality (i.e., octane) was the required specification and was consequently held fixed; in this example, isomerate product quality is allowed to vary (i.e., the ratio of 3MP and 23DMB in the effluent stream is allowed to vary). The product motor octane value was higher in the stacked bed system than in either the sole calcium 5A or the sole hydrogen ferrierite adsorption system. A larger bed size is required as product motor octane increases due to the associated higher rate of recycle (of 3MP) to the isomerization zone.

TABLE III

If requirement is an isomerate product stream of all-branched material (i.e., 23 DMB + 3MP)

|  | Ca-5A | H Ferrierite | Ca-5A/H-Ferr (1:4 Wt Ratio) |
|---|---|---|---|
| Quantity of Sieve Required to Yield 1.0 g of Product | 5.1 g | 17 g | 24 g |
| Product 23DMB:3MP Wt. Ratio | 1:1 | 1.5:1 | 2.3:1 |
| Product Motor Octane Value | 84.3 | 87.3 | 90.9 |

We claim as our invention:

1. An isomerization process to produce an isomerate product stream comprising a gasoline blending component from a hydrocarbon stream comprising $C_6$ normal paraffin, $C_6^+$ normal paraffins or mixtures thereof, said process comprising the combinative steps of:
    (a) passing said paraffin or mixtures of paraffins to an isomerization zone maintained at isomerization conditions and containing an isomerization catalyst to produce an isomerization zone effluent stream comprising di-branched paraffins, mono-methyl-branched paraffins, and unreacted normal paraffins;
    (b) passing said isomerization zone effluent stream to a separation zone containing multiple crystalline molecular sieves, each having pore sizes of different dimensions, wherein the first of said sieves has pores of a dimension effective to adsorb normal paraffins while being restrictive to prohibit adsorption of mono-methyl-branched paraffins and di-branched paraffins and wherein the second of said sieves has a pore size intermediate 5.5×5.5 and 4.5×4.5 A and is effective to adsorb normal paraffins and mono-methyl-branched paraffins while restrictive to prohibit adsorption of di-branched paraffins;
    (c) contacting said isomerization zone effluent stream with said first sieve in said separation zone to separate said n-paraffins from said mono-methyl-branched paraffins and di-branched paraffins, recovering and recycling at least a portion of said n-paraffins to said isomerization zone and forming a first sieve effluent stream comprising di-branched paraffins and mono-methyl-branched paraffins;
    (d) contacting said first sieve separation effluent stream with said second sieve to separate said di-branched paraffins from said mono-methyl-branched paraffins and to form an isomerate product stream comprising said di-branched paraffins as said gasoline blending component and, recovering and recycling at least a portion of said mono-methyl-branched paraffins to said isomerization zone.

2. The process of claim 1 wherein said isomerization conditions include a temperature of from about 200°-400° C. and a pressure of from about 10 bar to about 40 bar.

3. The process of claim 1 wherein said isomerization catalyst comprises an aluminosilicate having a Group VIII metal dispersed thereon.

4. The process of claim 3 wherein said aluminosilicate is mordenite and said Group VIII metal is platinum.

5. The process of claim 4 wherein said platinum is present in a weight concentration of from about 0.2 to about 0.4 weight percent.

6. The process of claim 4 wherein said mordenite has associated therewith an inorganic binder.

7. The process of claim 1 wherein said second molecular sieve comprises a ferrierite aluminosilicate having pore size intermediate 5.5×5.5 and 4.5×4.5 A.

8. The process of claim 1 wherein said first molecular sieve comprises calcium 5A aluminosilicate having pores of smaller dimension than said second sieve.

9. The process of claim 1 wherein said second molecular sieve comprises a tectosilicate having pore sizes intermediate 5.5×5.5 and 4.5×4.5 A, which tectosilicate has cations exchanged therewith selected from the group consisting of an alkali metal, an alkaline earth metal and transition metal cations.

10. The process of claim 1 wherein said di-branched paraffins comprise 2,3-dimethylbutane.

11. A process for the isomerization of a $C_6$ normal paraffin, $C_6^+$ normal paraffins or mixtures thereof to produce an isomerate gasoline blending component comprising di-branched paraffins, which process comprises:
    (a) passing said paraffin or mixture of paraffins to an isomerization zone maintained at isomerization conditions and containing an isomerization catalyst to isomerize said $C_6$ normal paraffin or mixture of $C_6^+$ normal paraffins and a hereinafter defined recycle stream to produce an isomerization zone effluent stream comprising di-branched paraffins, mono-methyl-branched paraffins and unreacted normal paraffins;
    (b) passing said isomerization zone effluent stream to a separation zone comprising multiple shape-selective molecular sieves arranged in a series flow path, wherein said isomerization zone effluent stream passes in contact with a first of said shape-selective molecular sieves and then passes in contact with a second of said shape-selective molecular sieves, wherein said multiple shape-selective molecular sieves comprise:
        (i) a first separatory molecular sieve having a pore size of 4.5 A or less and being effective to adsorb n-paraffins and effective to restrict adsorption of mono-methyl-branched paraffins and di-branched paraffins; and
        (ii) a second separatory molecular sieve having a pore size intermediate 5.5×5.5 and 4.5×4.5 A but excluding 4.5×4.5 A and being effective to adsorb n-paraffins and mono-methyl-branched paraffins and effective to restrict adsorption of di-branched paraffins;
    (c) separating said normal paraffins from said mono-methyl-branched paraffins and from said di-branched paraffins with said first shape-selective molecular sieve, recovering and recycling at least a portion of said n-paraffins to said isomerization zone of step (a) and passing said mono-methyl-branched paraffins and di-branched paraffins to said second shape-selective molecular sieve; and (d) separating said di-branched paraffins from said mono-methyl-branched paraffins in said second shape-selective molecular sieve, recovering said di-branched paraffins as said isomerate gasoline blending component and recovering and recycling at least a portion of said mono-methyl-branched paraffins to said isomerization zone of step (a).

12. The process of claim 11 wherein said isomerization conditions include a temperature of from about 200° C. to about 400° C. and a pressure of from about 10 bar to about 40 bar.

13. The process of claim 11 wherein said gasoline blending component comprises predominantly di-branched paraffins.

14. The process of claim 11 wherein said second shape-selective molecular sieve comprises ferrierite.

15. The process of claim 11 wherein said first shape-selective molecular sieve comprises a calcium 5A aluminosilicate.

16. The process of claim 11 wherein said normal paraffins recovered from said first shape-selective molecular sieve and said mono-methyl-branched paraffins recovered from said second shape-selective molecular sieve are admixed, prior to recycle of said normal paraffins and said mono-methyl-branched paraffins to said isomerization zone in step (a).

17. The process of claim 11 wherein said isomerization catalyst comprises a mordenite aluminosilicate with platinum metal dispersed thereon.

18. The process of claim 11 wherein said isomerization catalyst comprises a Y-faujausite aluminosilicate having 0.2 to 0.4 weight percent platinum dispersed thereon.

19. The process of claim 11 wherein said $C_6$ normal paraffin is normal hexane, said mono-methyl-branched paraffins are 3-methylpentanes and 2-methylpentanes and said di-branched paraffins are dimethylbutanes.

20. The process of claim 11 wherein said passage of isomerization zone effluent is made with said first and second separatory molecular sieves in a vertical relationship, wherein said isomerization zone effluent contacts said first separatory molecular sieve located below said second separatory molecular sieve.

21. The process of claim 11 wherein said passage of isomerization zone effluent is made with said first and second separatory sieves in a vertical relationship, wherein said isomerization zone effluent contacts said first separatory molecular sieve located above said second separatory molecular sieve.

22. The process of claim 11 wherein said passage of isomerization zone effluent is made with said first and second separatory sieves in a horizontal relationship, wherein said isomerization zone effluent contacts said first separatory molecular sieve situated juxtaposed to said second separatory molecular sieve.

* * * * *